United States Patent [19]

Dureanleau et al.

[11] Patent Number: 4,678,857

[45] Date of Patent: Jul. 7, 1987

[54] PROCESS FOR SEPARATION OF PRODUCT RESULTING FROM HYDROFORMYLATION

[75] Inventors: Roger G. Dureanleau, Georgetown; John F. Knifton, Austin, both of Tex.

[73] Assignee: Texaco Inc., White Plains, N.Y.

[21] Appl. No.: 846,543

[22] Filed: Mar. 31, 1986

[51] Int. Cl.$^4$ .............................................. C07C 45/50
[52] U.S. Cl. .................................. 568/454; 568/449; 568/482; 568/492; 568/909
[58] Field of Search ............... 568/449, 454, 492, 909, 568/482

[56] References Cited

U.S. PATENT DOCUMENTS

| | | | |
|---|---|---|---|
| 3,929,915 | 12/1975 | Cumbo et al. | 568/862 |
| 3,980,670 | 9/1976 | Kummer et al. | 549/326 |
| 3,980,671 | 9/1976 | Fernholtz | 549/326 |
| 4,064,145 | 12/1977 | Taylor | 568/454 |
| 4,083,882 | 4/1978 | Taylor | 568/454 |
| 4,400,548 | 8/1983 | Abatjugleau | 568/454 |
| 4,400,549 | 8/1983 | Richter | 568/454 |
| 4,567,305 | 1/1986 | Matsumoto et al. | 568/454 |

FOREIGN PATENT DOCUMENTS 1493154 8/1974 United Kingdom ................ 568/454

*Primary Examiner*—Werren B. Lone
*Attorney, Agent, or Firm*—Jack H. Park; Kenneth R. Priem; Cynthia L. Kendrick

[57] ABSTRACT

A process is disclosed for preparing products such as 4-hydroxybutanal which comprises contacting unsaturated compounds such as allyl alcohol with carbon monoxide and hydrogen in the presence of a rhodium carbonyl-phosphine catalyst and an aromatic solvent. The solvent is an aromatic which causes a large density difference between the resulting aqueous phase and organic phase so that the soluble rhodium catalyst can be easily separated from the 4-hydroxybutanal product and starting material without appreciable loss of the metal. This allows for easy recycle of the catalyst solution.

10 Claims, No Drawings

PROCESS FOR SEPARATION OF PRODUCT RESULTING FROM HYDROFORMYLATION

BACKGROUND OF THE INVENTION

1. Field of the Invention

This invention is related to the addition of hydrogen and carbon monoxide to allyl alcohol to obtain 4-hydroxybutanal in the presence of a catalyst comprising a rhodium carbonyl catalyst with excess phosphine and is more particularly related to such a reaction conducted in the presence of a particular solvent which allows recovery of the product by water extraction, leaving the rhodium catalyst solution behind. Such a system provides excellent separation of the product from the phase containing the expensive rhodium catalyst. Only trace amounts of rhodium are lost to the product-containing phase.

2. Description of Related Processes in the Field

The compound 4-hydroxybutanal is an important intermediate for producing 1,4-butanediol. A number of methods have been discovered for hydroformylating various unsaturated compounds such as allyl alcohol to useful products such as 4-hydroxybutanal.

U.S. Pat. No. 3,980,670 discloses a process for manufacturing methacrylic acid and butyrolactone by hydroformylation of allyl esters of lower carboxylic acids in the presence of rhodium carbonyl complex catalysts and inert organic solvents, followed by oxidation of the resulting formyl compounds with molecular oxygen to produce 4-acetoxy-n-butyric acid and 3-acetoxy-isobutyric acid as the major products. See also German Offen. No. 2,106,243 to BASF. Unsaturated compounds such as propylene may be hydroformylated by means of rhodium/triphenylphosphine/carbonyl complexes formed in situ using a special preforming step described in U.S. Pat. No. 4,400,549.

In an article entitled "1,4-Butanediol via Hydroformylation of Allyl Alcohol", Chem. Systems; PERP 4th Quarterly Report, April 1982, there is disclosed a process for producing 1,4-butanediol via gas-phase hydroformylation of allyl alcohol using a supported liquid phase metal-organic catalyst. This reaction involves four steps.

In U.S. Pat. No. 3,929,915 there is disclosed a 3-step process for preparing 1,4-butanediol wherein the starting material is acrolein; the reaction conditions are conventional and several intermediate compounds are formed.

Even more on point is the following patent, U.S. Pat. No. 4,064,145, which describes a method for producing tetrahydrofuran and 1,4-butanediol by reacting synthesis gas with allyl alcohol under hydroformylation conditions in the presence of a rhodium carbonyl-phosphine catalyst complex and various inert solvents such as organic aromatics, aliphatic hydroxylic organic solvents, etc. In this patent, the allyl alcohol conversion was reported to be 99% and 4-hydroxybutanal was typically obtained in 87 wt% yield. Here there is not a desirable level of accounting for the rhodium catalyst. Also the amount of triphenylphosphine used, compared to the solvent and catalyst, is fairly large. Additionally, with the solvent used in this case two steps are necessary for extraction. The major by-product was 2-methyl-3-hydroxypropanal (12 wt%). A rhodium catalyst complexed with special bisphosphine monoxide ligands is taught as catalyzing the hydroformylation of olefinic compounds in the presence of an organic solvent according to U.S. Pat. No. 4,400,548. Again, two phase solvent systems are not disclosed.

U.S. Pat. No. 4,221,726 discloses a process for producing 1,4-butanediol by selectively hydrogenating acrolein to a product mixture of allyl alcohol and residual acrolein in a 2:1 ratio, converting the mixture to acrolein diallyl acetal under acidic conditions, selectively hydroformylating the acrolein diallyl acetal to a trialdehyde and reacting the trialdehyde under substantially neutral hydrolysis/hydrogenation conditions to yield 1,4-butanediol.

In *J. Org. Chem.*, Vol. 45 (1980), 2132, C. U. Pittman, Jr. et al. disclose the hydroformylation of allyl alcohol to 4-hydroxybutanal and 3-hydroxy-2-methylpropanal using $HRh(CO)(PPh_3)_3$ and its polymer-bound analogues. The selectivity of normal/ branched products was studied as the function of reaction parameters and ligands employed. The highest normal/branched selectivities were reported with 1,1'-bis(diphenylphosphino)-ferrocene at 80%. Hazardous benzene and o-xylene solvents were generally used.

In *J. of Mol. Cat.*, Vol. 11 (1981), 233–246, N. A. deMunck reported a heterogeneous gas phase hydroformylation of allyl alcohol using a supported $HRh(CO)(PPh3)3$ catalyst. A very high selectivity to 4-hydroxybutyraldehyde (97%) was achieved. However, the process is limited to only about 20% allyl alcohol conversion.

Kuraray disclosed the hydroformylation of allyl alcohol using a rhodium catalyst in an organic solvent such as benzene and toluene and a diphosphinoalkane. The overall n-/iso-ratio of the products was 86.6/13.4, (Kuraray, Japan. Pat. Open. No. 29412/1976, and No. 106407/1979. In additional patents (Kuraray, Japan. Pat. Open, No. 84508/1979 and British Patent No. 1,493,154, 1977) to Kuraray, a modified Raney catalyst was claimed for the hydrogenation of hydroxybutyraldehydes into 1,4-butanediol and 2-methyl-1,3-propanediol.

It is known in the art that allyl alcohol can be hydroformylated to γ-hydroxybutyraldehyde in an aromatic hydrocarbon solution containing a rhodium complex catalyst and large excess of triphenylphosphine. The reaction products are extracted continuously with water and fed into a hydrogenation reactor containing a modified Raney nickel catalyst where the aldehydes are converted to corresponding alcohols, including 1,4-butanediol. See M. Tamura and S. Kumani; Chem. Econ. & Eng., Rev.; 12 #9 Sept. 1980; p. 32.

Many of the systems described above lack good conversions of the unsaturated reactant compound and/or good selectivity to the desired product. Further, recovery of expensive rhodium catalysts is a problem in many of these processes. It would be an advance in the art if a method could be devised for hydroformylating compounds such as allyl alcohol, while simultaneously solving the conversion, selectivity and catalyst recovery problems, and at the same time allowing isolation of the desired aldehyde product in reasonable purity and rate.

SUMMARY OF THE INVENTION

The invention concerns a process for preparing 4-hydroxybutanal which comprises hydroformylating allyl alcohol by reaction with carbon monoxide and hydrogen. A rhodium catalyst and a solvent are employed. The solvent is an aromatic compound which allows rapid separation of the 4-hydroxybutanal product from the rhodium catalyst when water extraction is used. The product may then be further converted to 1,4-butanediol without additional purification.

DESCRIPTION OF THE PREFERRED EMBODIMENTS

In general, the components of the hydroformylation reaction mixture, including the solvents, allylically unsaturated compound and rhodium catalyst may be added in any sequence as long as good agitation is employed to provide a good dispersion or a homogeneous reaction mixture. For example, the following represent some variations insofar as the addition of catalyst components, inert solvents and allyl alcohol addition that can be made without departing from the inventive process. These modifications include:

1. The catalyst may be preformed and added to the solvent prior to addition of the allyl alcohol and inert solvent components.

2. Alternatively, to minimize stability problems with the catalyst, the catalyst is formed in situ, usually by mixing the inert solvents and allyl alcohol, followed by the addition of the catalyst components to form the reaction mixture.

3. After using either variation 1 or 2, the deoxygenated catalyst-containing reaction mixture is pressurized with CO and hydrogen and heated until the 4-hydroxybutanal product is formed.

A rhodium catalyst is used in the present invention. Any rhodium-containing compound capable of forming a carbonyl compound under the reaction conditions can be used. This rhodium compound may, be a carbonyl such as hexarhodium hexadecylcarbonyl. Preferably, the rhodium carbonyl is complexed with a phosphine ligand. Such catalysts are described in U.S. Pat. Nos. 4,064,145; 4,400,548 and 4,400,549, the pertinent portions of which are herein incorporated by reference. It is preferred that the catalyst be a rhodium carbonyl triphenylphosphine complex catalyst such as hydridocarbonyltris(triphenylphosphine)rhodium(I). This complex may be written as HRh(CO)(PPh3)3, where Ph represents a phenyl group. Preferably, an excess of the phosphine ligand particularly triphenylphosphine, is added to provide a more stable catalyst system.

The method of this invention may be expected to be useful to hydroformylate many kinds of allylically-substituted unsaturated compounds. Suitable allylic compounds include allyl alcohol, alkyl-substituted allylic alcohols, alkyl allylic ethers such as methylallyl ether, ethylallyl ether and allyloctyl ether, as well as allylic esters such as allyl acetate, allyl propionate and allyl formate. The preferred reactant is allyl alcohol.

This invention allows practical use of allyl alcohol as a feed for making 1,4-butanediol via a hydroformylation route. The hydroformylation of allyl alcohol produces the intermediate 4-hydroxybutanal (eq. I) which is thermally unstable. This material (4-hydroxybutanal) must be separated from the catalyst, then hydrogenated to 1,4-butanediol (eq. II) without exposure to greater than 90° C. since it degrades rapidly at that temperature.

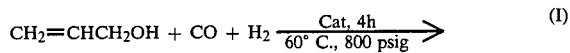

(I)

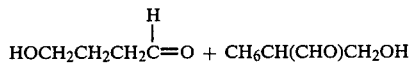

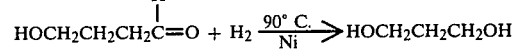

(II)

As noted, a novel feature of the invention is the choice of solvent. In a continuous run system, after addition of the water to the reaction stream, the organic and aqueous phases must disengage rapidly to minimize equipment expense used for the separation. The soluble rhodium is retained in the organic solvent allowing easy recycle of the catalyst, and the 4-hydroxybutanal intermediate is extracted in the aqueous phase.

The use of these solvents allows water extraction of 4-hydroxybutanal and subsequent hydrogenation of the aqueous solution without further purification. During this extraction the soluble rhodium catalyst is retained in the solvent allowing easy recycle of this catalytic solution. Because the active ingredient in the catalyst system is rhodium, a very expensive metal, the water layer must not contain more than traces of this metal. The instant invention demonstrates accounting for the rhodium catalyst to a degree not demonstrated in prior work. Any amounts of rhodium in the aqueous layer may be lost during the hydrogenation and separation prior to hydrogenation is impractical. Rhodium recovery after hydrogenation is also impractical in most cases. This disclosure identifies several solvent classes which meet these criteria.

Conversion of the aqueous solution extract, rich in 4-hydroxybutanal, to 1,4-butanediol is readily accomplished by methods already reported in the literature. See, for example, Chem. Systems Report 83-2, December 1983, entitled "1,4-Butanediol", and references therein.

We have observed that a variety of solvents are compatible with the rhodium catalyzed hydroformylation of allyl alcohol insofar as the reaction is concerned, but that the separation characteristics during the extraction phase indicate only a modest number of such solvents would be useable in a commercial process. Solvents containing the aromatic function appear to work best. To obtain the desired separation and reaction characteristics, it is believed a large density differential between the solvent and water is desirable.

Solvents that appear to fit these criteria include:

(a) Halogenated aromatic alkyl ether solvents such as 4-chloroanisole, 2-chloroanisole and 4-bromoanisole (Density, d=1.50), as well as 2-bromoanisole (d=1.50).

(b) Halogenated aromatic solvents such as chlorobenzene, 1,2-dichlorobenzene (d=1.31), 1,2,4-trichlorobenzene (d=1.57) and dibromonaphthalenes.

(c) Halogenated ethers such as bis(2-chloroethyl)ether (d=1.22).

(d) Halogenated aliphatics such as chloroform (d=1.50).

(e) Aromatics such as benzene, toluene and the xylenes, as well as tetralin.

(f) Aromatic ethers such as diphenyl ether.

(g) Aryl-containing ketones such as acetophenone.

The preferred class of solvents for the desired synthesis, which give good yields of desired 4-hydroxybutanal and efficient separation of this aldehyde from the rhodium-carbonyl-phosphine catalyst, is the halogenated aromatic alkyl ethers such as 4-bromoanisole and 4-chloroanisole.

The temperature range which can be employed for hydroformylation is a variable which is dependent upon experimental factors including the particular allylically unsaturated compound employed, the total pressure, the mole ratio of hydrogen and carbon monoxide used, the concentrations of reactants and catalyst, among other things. Using allyl alcohol as the substrate and rhodium carbonyl-triphenylphosphine complex as a representative catalyst, an operable range is from about 20° C. to 160° C. or more when superatmospheric pressures of greater than 100 psig are employed. A narrower range of 50° C. to 110° C. represents the preferred temperature range when the aforementioned allyl alcohol is hydroformylated.

The pressure range which can be employed for hydroformylation is a variable which is also dependent on the factors mentioned above. Using hydridocarbonyltris(triphenylphosphine)rhodium(I) as a representative catalyst and allyl alcohol as the substrate, an operable pressure range is from about 1 atm to 650 atm or more, with a mole ratio of $H_2/CO$ being 1:1 when a temperature range of from about 25° C. to 125° C. is employed. A narrower range of from 5 atm to 100 atm represents the preferred pressure range when the narrower temperature range of 50° C. to 110° C. is employed.

The temperature and pressure conditions employed for the separation of the product from the catalyst are 1 atm, at greater than 0° C. to 40° C.

The $H_2/CO$ mole ratio may be varied over a range of from 30:1 to 1:30 when suitable temperatures and pressures are employed. A preferred narrower range is from 2:1 to 1:2 of hydrogen/carbon monoxide.

Experimental variables are important in arriving at reaction times. Generally, substantial conversions (80% or higher) of the allyl alcohol to 4-hydroxybutanal can almost always be accomplished within 18 hours, with 2 to 6 hours representing the more usual reaction time interval.

Experimental work indicates that an initial molar ratio of 10 moles to 10,000 moles of allyl alcohol per mole of rhodium-containing catalyst complex can be employed in most instances. The minimal ratio of 0.0001 moles of catalyst per mole of allyl alcohol is herein referred to as a "catalytic ratio" or "catalytic amount". Much higher ratios (i.e., 25 moles of substrate per mole of rhodium catalyst complex) are not harmful but are economically unattractive. For this reason the favored mole ratio ranges from 50 to 5,000 moles of allyl alcohol per mole of rhodium catalyst complex.

Using the process of this invention, at least 90 wt. % of the catalyst should be present in the resulting upper, water phase and at least 90 wt. % of the 4-hydroxybutanal product should be present in the lower, solvent phase.

Allyl alcohol hydroformylation products, such as 4-hydroxybutanal, may also be isolated by the usual chemical or physical techniques, such as distillation, chromatography, etc. Identification is by nuclear magnetic resonance and/or gas-liquid chromatography (glc).

Conversion as defined herein represents the extent of conversion of the reacting allyl alcohol to other products. Conversion is expressed as a percentile and is calculated by dividing the amount of allyl alcohol consumed during hydroformylation by the amount of alcohol originally charged and multiplying the quotient by 100. The allyl alcohol conversion in the process of this invention can be at least 90%.

Yield, as defined herein, represents the efficiency in catalyzing the desired hydroformylation reaction relative to other undesired reactions. In this instance hydroformylation to 4-hydroxybutanal is the desired conversion. Yield is expressed as a percentile and is calculated by determining the molar amount of 4-hydroxybutanal product formed, divided by the molar amount of allyl alcohol charged and multiplying the quotient obtained by 100.

Selectivity, as defined herein, is the efficiency in catalyzing a desired hydroformylation reaction relative to the other undesired conversions. Selectivity is expressed as a percentile and is calculated by determining the amount of 4-hydroxybutanal product formed, divided by the total amount of $C_4$ products formed and multiplying the quotient obtained by 100. Selectivity can be at least 90% for the inventive process.

Having described the inventive process in general terms, the following examples are submitted to supply specific and illustrative embodiments of the improved process of the instant invention.

EXAMPLE 1

A 300 ml stainless steel pressure vessel equipped with a magnetic stirrer and capable of operating at 5,000 psig was charged with allyl alcohol, (30 ml =25.62g =441 mmoles), triphenylphosphine (1.75g =6.68 mmoles), hydridocarbonyltris(triphenylphosphine)rhodium(I) (0.153g =0.167 mmoles), along with chlorobenzene (20.0 ml =22.1g =196.5 mmoles). The vessel was then flushed with syngas ($CO/H_2=1/1$), heated to 60° C. then pressured to 800 psig while stirring continuously. These conditions were maintained for 4 hours (60° C., 800 psig const. press., stirring) then the system was cooled, dismantled and the contents collected after a gas sample was obtained. The reaction product (59.6g) was treated with 50.0g of water, thoroughly mixed in a funnel and the layers separated. Separation was nearly complete after 25 minutes but 16 hours were allowed to finish the separation.

Each layer was sampled, then all liquid samples were analyzed for rhodium by atomic absorption techniques. Gas samples were analyzed by glc techniques.

The crude liquid product mixture contained:
1.57% unreacted allyl alcohol
0.2% methacrolein
2.25% triphenylkphosphine +triphenylphosphine oxide
93.7% chlorobenzene +4-hydroxybutanal
The concentration of rhodium in the crude liquid product =260 ppm.

After water extraction, the aqueous layer (96.0g) showed the presence of:
38.0% 4-hydroxybutanal
<1% chlorobenzene
60.4% water
4.94 ppm rhodium Analysis of the organic phase showed the presence of:
1.6% allyl alcohol
93.7% chlorobenzene +hydroxybutanal
1.0% water
668 ppm rhodium The estimated conversion of allyl alcohol in this experiment =95%.

The estimated yield of 4-hydroxybutanal in the aqueous extract =94%.

Typical gas analysis showed:

48.5% hydrogen
50.1% carbon monoxide

These data clearly illustrate that this solvent, chlorobenzene, is an acceptable reaction medium both for the synthesis of 4-hydroxybutanal from allyl alcohol, and for the rhodium-phosphine catalyst. Furthermore, recovery of the desired 4-hydroxybutanal can be achieved in 94% yield after only one aqueous extraction.

EXAMPLE 2

Following the procedures of Example 1, the reactor was charged with a mixture of:
Allyl alcohol (30 ml, 441 mmole)
Triphenylphosphine (1.75g, 6.68 mmole)
Hydridocarbonyl tris(triphenylphosphine)rhodium(I) (0.153g, 0.167 mmole)
4-bromoanisole (20.0 ml, 31.2g, 155.7 mmole)

The reaction was conducted at 60° C., with CO/H$_2$ (1:1) at 800 psig, conditions were maintained for 4 hours. Analysis of the crude liquid product showed the presence of:
60.5% 4-hydroxybutanal
35.5% 4-bromoanisole
2.24% triphenylphosphine + triphenylphosphine oxide
<1% unreacted allyl alcohol The estimated yield of 4-hydroxybutanal =98.7%
The concentration of rhodium in the crude liquid product =122 ppm This crude liquid product (59.6g) was treated with water (20.0g), and phase separation was rapid and complete within 15 minutes. Analysis of the aqueous phase showed the presence of:
40.8% 4-hydroxybutanal
0.3% 4-bromoanisole
56.6% water
<10 ppm rhodium Analysis of the organic phase showed the presence of:
<0.1% allyl alcohol
0.4% 4-hydroxybutanal
0.17% water
89.3% 4-bromoanisole
228 ppm rhodium The estimated conversion of allyl alcohol in this experiment = >99%
The estimated yield of 4-hydroxybutanal in the aqueous extract = >98%

These data clearly show that 4-bromoanisole is an acceptable reaction medium both for the synthesis of 4-hydroxybutanal from allyl alcohol, and for the rhodium phosphine catalyst. Furthermore, rapid recovery of the desired 4-hydroxybutanal can be achieved in >98% yield after only one aqueous extraction.

EXAMPLES 3–10

A series of other aromatic solvents have been evaluated for the synthesis of 4-hydroxybutanal using the homogeneous rhodium-phosphine catalyst. These solvents include examples of:
(a) Halogenated aromatic alkyl ether solvents, such as 4-chloroanisole.
(b) Halogenated aromatic solvents such as 1,2-dichlorobenzene.
(c) Halogenated ethers such as bis(2-chloroethyl)ether.
(d) Aromatics such as tetralin and xylenes.
(e) Aromatic ethers such as diphenyl ether.
(f) Aryl-containing ketones such as acetophenone.

Of particular note:

In Example 3, using anisole as solvent, the phases were nearly the same density, the 4-hydroxybutanal was obtained in high yield, allyl alcohol conversion was >98% and the phase separation time was acceptable (50-60 minutes).

In Example 4, using acetophenone, the phase separation time was 50+ hours.

In Example 5, using tetralin as solvent, the separation was not at all adequate, requiring three days.

Using xylene, in Example 6 the separation took about four hours and was poor and difficult.

Bis-2-chloroethylether produced good partition and rapid separation in about 15 minutes, as shown in Example 7. Furthermore, allyl alcohol conversion was Ca. 87% and 4-hydroxybutanal yields were good.

In Example 8, using chloroanisole, a slower separation at the interphase was exhibited. The separation took about 40 minutes and some solvent was observed in the water.

In Example 9, using diphenyl ether, a third phase formed, separation was very slow, and conversion of allyl alcohol was lower.

In Example 10, with o-dichlorobenzene as solvent, isomerization of the aldehyde product was observed during glc analysis of the aqueous phase. Otherwise the system worked well and adequate phase separation took place in about eight minutes.

| | | | | | | | | First Water Extraction[b] | | | | |
| | | | | Reaction Product[b] | | | | Organic Phase | | | Water Phase | |
| Example | Solvent Name | Mmole Solvent | Rh (ppm) | % 4HB | % Solvent | % TPP & TPPO | % Conversion | Rh (ppm) | % 4HB | % H$_2$O | Rh (ppm) | % 4HB | % Solvent |
| --- | --- | --- | --- | --- | --- | --- | --- | --- | --- | --- | --- | --- | --- |
| 3 | Anisole | 184.2 | 290 | 58.42 | 34.46 | 2.28 | 98.6 | 774 | 6.55 | <0.1 | <1 | 41.1[c] | <0.5 |
| 4 | Acetophenone | 171.1 | 236 | 61.67 | 33.17 | 2.18 | 98.7 | 577 | 27.45 | 13.13 | 11.1 | 34.8 | 6.7 |
| 5 | Tetralin | 146.7 | 269 | 64.28 | 28.53 | 2.16 | 96.1 | 773 | 2.16 | <1 | 1.98 | 39.0 | — |
| 6 | Xylene | 162.8 | 243 | — | — | 2.45 | 90.8 | 226 | 51.55 | 4.97 | 81.6 | 5.4 | 21.2 |
| 7 | bis-2-chloroethyl ether | 170.6 | 143 | 45.37 | 36.31 | 2.04 | 86.9 | 362 | 9.85 | 2.04 | <1 | 30.86 | 4.09 |
| 8 | Chloroanisole | 168.4 | 227 | 55.5 | 40.74 | 1.58 | 99+ | 497 | 1.0 | 0.35 | 4.0 | 32.2 | 2.75 |
| 9 | Phenylether | 121.1 | 253 | 59.5 | 29.78 | 1.91 | 87.3 | — | — | — | — | — | — |
| 10 | o-dichloro- | 177.5 | 177 | 64.4 | 31.2 | 1.26 | 99.5 | 420 | 0.08 | 0.01 | <5 | 49.8 | 0.08 |

EVALUATION OF SOLVENTS FOR HYDROFORMYLATION OF ALLYL ALCOHOL[a]

| Example | Solvent Name | Mmole Solvent | Reaction Product[b] | | | | | First Water Extraction[b] | | | | | |
|---|---|---|---|---|---|---|---|---|---|---|---|---|---|
| | | | | | | | | Organic Phase | | | Water Phase | | |
| | | | Rh (ppm) | % 4HB | % Solvent | % TPP & TPPO | % Conversion | Rh (ppm) | % 4HB | % H$_2$O | Rh (ppm) | % 4HB | % Solvent |
| | benzene | | | | | | | | | | | | |

[a]Reaction Charge:
Allyl Alcohol 441 mmoles
triphenylphosphine 6.68 mmoles
Hydridocarbonyltris(triphenylphosphine)rhodium(I) 0.167 mmole
Reaction Conditions:
CO/H$_2$ = 1/1
Press. = 800 psig
Temp. = 60° C.
Time = 4 hours
[b]Designations:
4HB, 4-hydroxybutanal
TTPO, triphenylphosphine oxide
TTP, triphenylphosphine

EXAMPLE 11

A continuous run was conducted on a catalyst solution which had previously been activated. This catalyst solution was originally prepared by dissolving hydridocarbonyltris(triphenylphosphine)rhodium(I) and triphenylphosphine in p-bromoanisole. It comprised: 72% 4-bromoanisole, 10.9% 4-hydroxybutanal, 10.5% acetals, 1.3% triphenylphosphine +triphenylphosphine oxide, 1.6% water, 0.5% isobutanol, 3.2% unknowns and 340 ppm rhodium.

The same solution, plus allyl alcohol, were pumped separately to a 300 ml stainless steel stirred reactor at the rate of 30 ml/hr each. Excess syngas was introduced into the reactor at a rate of 100 l/hr. The prefilled reactor was brought to equilibrium (6 hr.) under the operating conditions of Example 1 (i.e. 80° C., 800 psi), and liquid samples withdrawn at 4 hr. intervals. Gas samples were removed every eight hours.

A typical liquid product effluent contained:

| p-bromoanisole | 32.7% |
|---|---|
| 4-hydroxybutanal | 51.0% |
| allyl alcohol | 3.3% |
| acetals | 5.55 |
| triphenylphosphine & oxide | 1.25% |
| water | 0.56% |
| unknowns | 5.69% |
| rhodium | 139 ppm |

The combined fractions from the run (including unused samples) were extracted with an equal volume of water. The layers separated well in about 6 minutes. Each of the layers were analyzed by the usual gc method. The water layer contained:

| water | 73.0% |
|---|---|
| allyl alcohol | 2.6% |
| 4-hydroxybutanal | 21.2% |
| isobutanol | 0.5% |
| 1,4-butanediol | 0.5% |
| rhodium | 0.3 ppm |
| unknowns | 2.2% |

The organic layer contained:

| water | 0.2% |
|---|---|
| p-bromoanisole | 80.7% |
| triphenylphosphine & oxide | 1.6% |
| 4-hydroxybutanal | 8.0% |
| acetals | 5.3% |
| isobutanol | 0.3% |
| allyl alcohol | 1.7% |
| rhodium | 380 ppm |
| unknowns | 1.2% |

From these data it is clear that allyl alcohol may be continuously hydroformylated to 4-hydroxybutanal in high yield and this product efficiently extracted at ambient conditions, with water, readily allowing recycle of the active rhodium catalyst solution.

The estimated conversion of allyl alcohol per pass =96.6%

The estimated yield of 4-hydroxybutanal per pass =95.5%

What is claimed is:

1. In a process for hydroformylation of allyl alcohol to 4-hydroxybutanal by reaction with carbon monoxide and hydrogen in the presence of a rhodium-containing catalyst with excess triphenylphosphine at a temperature in the range of from about 50° to 110° C. and at a pressure in the range from about 5 atm to 100 atm, the improvement comprising using a solvent from the group consisting of halogenated aromatic alkyl ethers, halogenated aromatics, halogenated ethers, halogenated aliphatic solvents, and aromatic solvents from the group consisting of benzene, toluene, tetralin and mixed xylenes which preferably exhibit a large density differential compared with water, thus allowing rapid separation of the aqueous phase and organic phase, as well as improved selectivity and yield of the desired 4-hydroxybutanal product.

2. The process of claim 1 wherein, after the synthesis of the 4-hydroxybutanal and treatment of the reaction mixture with water, said mixture separates into two phases, an aqueous phase and an organic phase, wherein at least 90 wt % of the rhodium catalyst is present in the organic phase and at least 60 wt % of the 4-hydroxybutanal product is present in the aqueous phase.

3. The process of claim 1 in which the catalyst precursor comprises hydridocarbonyltris(triphenylphosphine)rhodium and excess triphenylphosphine.

4. The process of claim 1 wherein the halogenated aromatic alkyl ether solvent is selected from the group consisting of 4-bromoanisole, 4-chloroanisole and 2-chloroanisole.

5. The process of claim 1 wherein the halogenated aromatic solvent is selected from the group consisting of chlorobenzene, 1,2-dichlorobenzene, and 1,2,4-trichlorobenzene.

6. The process of claim 1 wherein the halogenated ether solvent is bis(2-chloroethyl)ether.

7. The process of claim 1 wherein the aromatic ether solvent is diphenyl ether.

8. The process of claim 1 wherein the aryl-containing ketone solvent is acetophenone.

9. The process of claim 2 wherein aqueous and organic phases form and at least 95 wt % of the rhodium catalyst is present in the organic phase and at least 90 wt % of the 4-hydroxybutanal product is present in the aqueous phase.

10. A process for separating 4-hydroxybutanal prepared by hydroformylating allyl alcohol by reaction with carbon monoxide and hydrogen in the presence of a rhodium carbonyl-triphenylphosphine complex catalyst which comprises using a solvent consisting essentially of p-bromoanisole wherein, after the reaction and treatment with water, the mixture separates into two liquid phases, an organic phase and an aqueous phase where at least 90 wt % of the rhodium catalyst is present in the organic phase and at least 90 wt % of the 4-hydroxybutanal is present in the aqueous phase, allyl alcohol conversion being at least 90% and 4-hydroxybutanal yield being at least 90%, wherein the process is conducted at a temperature in the range of from about 50° to 120° C. and at a pressure in the range of from about 5 atm to 100 atm.

* * * * *